US010581558B2

(12) United States Patent
    Cao

(10) Patent No.: US 10,581,558 B2
(45) Date of Patent: Mar. 3, 2020

(54) DATA TRANSMISSION METHOD AND APPARATUS, AND FIRST DEVICE

(71) Applicant: Huawei Technologies Co., Ltd., Shenzhen (CN)

(72) Inventor: Qingfeng Cao, Xi'an (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 94 days.

(21) Appl. No.: 15/550,702

(22) PCT Filed: Feb. 11, 2015

(86) PCT No.: PCT/CN2015/072752
    § 371 (c)(1),
    (2) Date: Aug. 11, 2017

(87) PCT Pub. No.: WO2016/127336
    PCT Pub. Date: Aug. 18, 2016

(65) Prior Publication Data
    US 2018/0026753 A1    Jan. 25, 2018

(51) Int. Cl.
    *H04L 1/18*      (2006.01)
    *G16H 10/60*     (2018.01)
    *H04L 29/08*     (2006.01)

(52) U.S. Cl.
    CPC .............. *H04L 1/18* (2013.01); *G16H 10/60* (2018.01); *H04L 69/324* (2013.01)

(58) Field of Classification Search
    None
    See application file for complete search history.

(56) References Cited

U.S. PATENT DOCUMENTS

| 8,105,208 B2 | 1/2012 | Oleson et al. |
| 10,327,639 B2 * | 6/2019 | Nagasaki ............... A61B 5/002 |
| 2003/0233250 A1 | 12/2003 | Joffe et al. |
| 2006/0206013 A1 | 9/2006 | Rothman et al. |
| 2007/0073545 A1 | 3/2007 | Tashiro |

(Continued)

FOREIGN PATENT DOCUMENTS

| CN | 1490756 A | 4/2004 |
| CN | 101515371 A | 8/2009 |

(Continued)

OTHER PUBLICATIONS

Machine Translation and Abstract of Japanese Publication No. JP2005261710, Sep. 29, 2005, 24 pages.

(Continued)

*Primary Examiner* — Jeffrey M Rutkowski
*Assistant Examiner* — Basil Ma
(74) *Attorney, Agent, or Firm* — Conley Rose, P.C.

(57) ABSTRACT

A data transmission method, apparatus, and a first device are provided in order to improve accuracy of analyzing sports and health data of a user. The method includes first storing, by a first device according to a particular data storage structure, sports and health data that is within a specified time period and that is detected by the first device, and then transmitting at least some of the sports and health data within the specified time period to a second device according to the data storage structure.

15 Claims, 4 Drawing Sheets

(56) References Cited

U.S. PATENT DOCUMENTS

| | | | | |
|---|---|---|---|---|
| 2009/0006920 | A1* | 1/2009 | Munson | H04L 1/0002 714/748 |
| 2011/0078572 | A1* | 3/2011 | Milazzo | G06F 11/34 715/733 |
| 2011/0098928 | A1* | 4/2011 | Hoffman | A63B 24/0062 702/5 |
| 2014/0379273 | A1* | 12/2014 | Petisce | G06F 19/00 702/19 |
| 2015/0018660 | A1 | 1/2015 | Thomson et al. | |
| 2015/0324541 | A1 | 11/2015 | Cheung et al. | |

FOREIGN PATENT DOCUMENTS

| | | |
|---|---|---|
| CN | 101879066 A | 11/2010 |
| CN | 103027752 A | 4/2013 |
| CN | 103959293 A | 7/2014 |
| JP | 2005142856 A | 6/2005 |
| JP | 2005261710 A | 9/2005 |
| JP | 2005527884 A | 9/2005 |
| JP | 2005295342 A | 10/2005 |
| JP | 2008276581 A | 11/2008 |
| JP | 2010165320 A | 7/2010 |

OTHER PUBLICATIONS

Machine Translation and Abstract of Japanese Publication No. JP2005295342, Oct. 20, 2005, 49 pages.
Machine Translation and Abstract of Japanese Publication No. JP2008276581, Nov. 13, 2008, 10 pages.
Machine Translation and Abstract of Japanese Publication No. JP2010165320, Jul. 29, 2010, 22 pages.
Foreign Communication From a Counterpart Application, Japanese Application No. 2017-542029, Japanese Notice of Reasons for Rejection dated Sep. 11, 2018, 3 pages.
Foreign Communication From a Counterpart Application, Japanese Application No. 2017-542029, English Translation of Japanese Notice of Reasons for Rejection dated Sep. 11, 2018, 5 pages.
Foreign Communication From a Counterpart Application, European Application No. 15881498.8, Extended European Search Report dated Jan. 25, 2018, 12 pages.
Machine Translation and Abstract of Chinese Publication No. CN1490756, Apr. 21, 2004, 9 pages.
Machine Translation and Abstract of Chinese Publication No. CN101515371, Aug. 26, 2009, 11 pages.
Machine Translation and Abstract of Chinese Publication No. CN101879066, Nov. 10, 2010, 23 pages.
Foreign Communication From a Counterpart Application, PCT Application No. PCT/CN2015/072752, English Translation of International Search Report dated Nov. 18, 2015, 2 pages.
Foreign Communication From a Counterpart Application, PCT Application No. PCT/CN2015/072752, English Translation of Written Opinion dated Nov. 18, 2015, 6 pages.
Machine Translation and Abstract of Chinese Publication No. CN103027752, Apr. 10, 2013, 32 pages.
Foreign Communication From a Counterpart Application, Chinese Application No. 201580068432.9, Chinese Office Action dated Apr. 3, 2019, 8 pages.

* cited by examiner

Sports state field structure:

| | | | Steps: 0 steps to 131071 steps | Calorie: 0 to 16777215 calories | Distance: 0 meters to 524287 meters | |
|---|---|---|---|---|---|---|
| Index 7 bits | Flag bits of primary and secondary frames 1 bit | Current status 7 bits | Step 17 bits | Calorie 24 bits | Distance 19 bits | Primary frame 75 bits |

| | | | Steps: 0 steps to 2047 steps | Calorie: 0 calories to 32767 calories | Distance: 0 meters to 4095 meters | |
|---|---|---|---|---|---|---|
| Index 7 bits | Flag bits of primary and secondary frames 1 bit | Current status 7 bits | Step 11 bits | Calorie 15 bits | Distance 12 bits | Secondary frame 53 bits |

Ratio for one primary frame and one secondary frame, 128 bits in total=16 bytes

Sleep state field structure:

| | | | Sleep deep: 0 minutes to 1440 minutes | Calorie: 0 calories to 16777215 calories | Sleep shallow: 0 minutes to 1440 minutes | |
|---|---|---|---|---|---|---|
| Index 7 bits | Flag bits of primary and secondary frames 1 bit | Current status 7 bits | Deep 17 bits | Calorie 24 bits | Shallow 19 bits | Primary frame 75 bits |

| | | | | Calorie: 0 calories to 32767 calories | | |
|---|---|---|---|---|---|---|
| Index 7 bits | Flag bits of primary and secondary frames 1 bit | Current status 7 bits | Reserved 11 bits | Calorie 15 bits | Reserved 12 bits | Secondary frame 53 bits |

Ratio for one primary frame and one secondary frame, 128 bits in total=16 bytes

0xFF: writable
0xFD: valid
0xF8: invalid
0x00: erasable

←——— 16 oct ———→

| Logical number 1 oct | Data overflow 1 oct | Logical page status 1 oct | Byte quantity of a data frame 2 oct | Time counter 4 oct | Reversed 7 oct | Primary frame 75 bits | Secondary frame 53 bits |
|---|---|---|---|---|---|---|---|

| Logical page Header 16 oct | One primary frame and one secondary frame 16 Oct | One primary frame and one secondary frame 16 Oct | -------- | One primary frame and one secondary frame 16 Oct |
|---|---|---|---|---|
| | First group | Second group | | $n^{th}$ group, n≤63 |

←— 16 oct —×——Maximum length: 16 oct * 63 = 1008 Oct——→
←————————Maximum length: 1024 oct————————→

DATA TRANSMISSION METHOD AND APPARATUS, AND FIRST DEVICE

CROSS-REFERENCE TO RELATED APPLICATION

This application is a U.S. National Stage of International Patent Application No. PCT/CN2015/072752 filed on Feb. 11, 2015, which is hereby incorporated by reference in its entirety.

TECHNICAL FIELD

The present disclosure relates to the field of information technologies, and in particular, to a data transmission method and apparatus, and a first device.

BACKGROUND

With rapid development of information technologies, more electronic devices are applied to various fields of life, and wearable devices come into being. A wearable device may first obtain sports and health data of a user, store the sports and health data of the user per fixed unit time, and then transmit the sports and health data of the user to a data server side in a wireless transmission manner using user equipment such as a mobile phone such that the data server side stores and analyzes the health data of the user.

However, when the wearable device stores the sports and health data of the user per fixed unit time, the wearable device needs to transmit sports and health data, which corresponds to each time period, of the user to the data server side in the wireless transmission manner using user equipment such as a mobile phone, for storage and analysis. Because a channel may be unstable during the wireless transmission, some of the sports and health data of the user may be lost during transmission. Consequently, a total amount, which is obtained through calculation, of the sports and health data of the user deviates, and accuracy of analyzing the sports and health data of the user is relatively low.

SUMMARY

The present disclosure provides a data transmission method and apparatus, and a first device in order to improve accuracy of analyzing sports and health data of a user.

Technical solutions used in the present disclosure are as follows.

According to a first aspect, the present disclosure provides a data transmission method, where the method includes storing, by a first device according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period, and transmitting, by the first device, at least some of the sports and health data within the specified time period to a second device according to the data storage structure.

With reference to the first aspect, in a first possible implementation of the first aspect, each logical page includes at least one data frame group, each data frame group includes one primary frame and at least one secondary frame, the primary frame records sports and health data detected within a second time period, the secondary frame records sports and health data detected within a third time period, the second time period is a corresponding time period obtained by adding a previous primary frame of the primary frame, the secondary frame, and the specified time interval to the start time of the specified time period, and the third time period is a time period obtained by adding the specified time interval to an end time of a previous primary frame of the secondary frame or to an end time of the secondary frame, where the end time is used as a start time.

With reference to the first possible implementation of the first aspect, in a second possible implementation of the first aspect, the specified time interval is a time corresponding to one primary frame or secondary frame.

With reference to the first aspect, the first possible implementation of the first aspect, or the second possible implementation of the first aspect, in a third possible implementation of the first aspect, the specified time period is divided into at least one time zone, the logical pages are in a one-to-one correspondence with the time zones in order, the time zone is recorded in a field of a timestamp of a corresponding logical page, and an accumulated time period of the timestamp is the specified time period such that the second device determines a lost logical page of the sports and health data according to the timestamp.

With reference to the first aspect, the first possible implementation of the first aspect, the second possible implementation of the first aspect, or the third possible implementation of the first aspect, in a fourth possible implementation of the first aspect, the method further includes receiving, by the first device, a retransmission request message sent by the second device, where content of the retransmission request message is empty, and the retransmission request message is used to indicate that the second device has not received sports and health data corresponding to a last logical page, or the retransmission request message carries a field of the last logical page, and the field of the last logical page is used to instruct the first device to retransmit sports and health data corresponding to the last logical page, and resending, by the first device, the sports and health data on the last logical page to the second device according to an indication of the retransmission request message.

With reference to the first aspect, the first possible implementation of the first aspect, the second possible implementation of the first aspect, the third possible implementation of the first aspect, or the fourth possible implementation of the first aspect, in a fifth possible implementation of the first aspect, transmitting, by the first device, at least some of the sports and health data within the specified time period to a second device according to the data storage structure further includes directly transmitting, by the first device, the sports and health data within the specified time period to the second device according to the data storage structure, or first storing, by the first device, the sports and health data within the specified time period according to the data storage structure and then transmitting the sports and health data within the specified time period to the second device.

According to a second aspect, the present disclosure provides another data transmission method, where the method includes receiving, by a second device, sports and health data that is sent by a first device according to a particular data storage structure, where the particular data storage structure is divided into at least one logical page, each logical page includes at least one data frame group, each data frame group includes one primary frame and at least one secondary frame, the primary frame records sports and health data detected within a first time period, and the secondary frame records sports and health data detected within a second time period.

With reference to the second aspect, in a first possible implementation of the second aspect, the logical page carries a timestamp, the timestamp records a start time of sports and health data stored on the logical page, and each data frame group includes one primary frame and at least one secondary frame. The method includes obtaining, by the second device, a system time corresponding to the second device, a start time corresponding to a timestamp on the last logical page, and a sum of quantities of primary frames and secondary frames on the last logical page, determining, by the second device, whether a difference between the system time corresponding to the second device and the start time corresponding to the timestamp on the last logical page is equal to a product of the sum of the quantities of the primary frames and the secondary frames on the last logical page and the second time period, and sending, by the second device, a retransmission request message to the first device if the second device determines that the difference between the system time corresponding to the second device and the start time corresponding to the timestamp on the last logical page is not equal to the product of the sum of the quantities of the primary frames and the secondary frames on the last logical page and the second time period, where the retransmission request message is used to indicate that the second device has not received sports and health data on the last logical page.

According to a third aspect, the present disclosure provides a data transmission apparatus, where the data transmission apparatus is a first device, and the first device includes a storage control unit configured to store, according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period, and a transmission control unit configured to control a transmitter according to the data storage structure to transmit at least some of the sports and health data within the specified time period to a second device.

With reference to the third aspect, in a first possible implementation of the third aspect, each logical page includes at least one data frame group, each data frame group includes one primary frame and at least one secondary frame, the primary frame records sports and health data detected within a second time period, the secondary frame records sports and health data detected within a third time period, the second time period is a corresponding time period obtained by adding a previous primary frame of the primary frame, the secondary frame, and the specified time interval to the start time of the specified time period, and the third time period is a time period obtained by adding the specified time interval to an end time of a previous primary frame of the secondary frame or to an end time of the secondary frame, where the end time is used as a start time.

With reference to the first possible implementation of the third aspect, in a second possible implementation of the third aspect, the specified time interval is a time corresponding to one primary frame or secondary frame.

With reference to the third aspect, the first possible implementation of the third aspect, or the second possible implementation of the third aspect, in a third possible implementation of the third aspect, the specified time period is divided into at least one time zone, the logical pages are in a one-to-one correspondence with the time zones in order, the time zone is recorded in a field of a timestamp of a corresponding logical page, and an accumulated time period of the timestamp is the specified time period such that the second device determines a lost logical page of the sports and health data according to the timestamp.

With reference to the third aspect, the first possible implementation of the third aspect, the second possible implementation of the third aspect, or the third possible implementation of the third aspect, in a fourth possible implementation of the third aspect, the transmission control unit includes a receiving module and a sending module, where the receiving module is configured to receive a retransmission request message sent by the second device, where content of the retransmission request message is empty, and the retransmission request message is used to indicate that the second device has not received sports and health data corresponding to a last logical page, or the retransmission request message carries a field of the last logical page, and the field of the last logical page is used to instruct the apparatus to retransmit sports and health data corresponding to the last logical page, and the sending module is configured to resend the sports and health data on the last logical page to the second device according to an indication of the retransmission request message received by the receiving module.

With reference to the third aspect, the first possible implementation of the third aspect, the second possible implementation of the third aspect, the third possible implementation of the third aspect, or the fourth possible implementation of the third aspect, in a fifth possible implementation of the third aspect, the apparatus directly transmits the sports and health data within the specified time period to the second device according to the data storage structure, or the apparatus first stores the sports and health data within the specified time period according to the data storage structure and then transmits the sports and health data within the specified time period to the second device.

According to a fourth aspect, the present disclosure provides another data transmission apparatus, where the apparatus includes a receiving unit configured to receive, in a second device, sports and health data that is sent by a first device according to a particular data storage structure, where the particular data storage structure is divided into at least one logical page, each logical page includes at least one data frame group, each data frame group includes one primary frame and at least one secondary frame, the primary frame records sports and health data detected within a first time period, and the secondary frame records sports and health data detected within a second time period.

With reference to the fourth aspect, in a first possible implementation of the fourth aspect, the logical page carries a timestamp, the timestamp records a start time of sports and health data stored on the logical page, and each data frame group includes one primary frame and at least one secondary frame. The apparatus includes an obtaining unit, a determining unit, and a sending unit, where the obtaining unit is configured to obtain, in the second device, a system time corresponding to the second device, a start time corresponding to a timestamp on the last logical page, and a sum of quantities of primary frames and secondary frames on the last logical page, the determining unit is configured to determine, in the second device, whether a difference between the system time corresponding to the second device and the start time corresponding to the timestamp on the last logical page that are obtained by the obtaining unit is equal to a product of the sum of the quantities of the primary frames and the secondary frames on the last logical page and the second time period, and the sending unit is configured to send, in the second device, a retransmission request message to the first device when the second device determines that the difference between the system time corresponding to the second device and the start time corresponding to the timestamp on the last logical page is not equal to the product of the sum of the quantities of the primary frames and the secondary frames on the last logical page and the second time period, where the retransmission request message is used to indicate that the second device has not received sports and health data on the last logical page.

According to a fifth aspect, the present disclosure provides a data transmission device, where the data transmission device is a first device, the first device includes a memory, a transmitter, and a processor, and the processor is connected to the memory and the transmitter using a data bus, where the processor is configured to store, in the memory according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period, and the processor is configured to transmit at least some of the sports and health data within the specified time period to a second device according to the data storage structure using the transmitter.

With reference to the fifth aspect, in a first possible implementation of the fifth aspect, each logical page includes at least one data frame group, each data frame group includes one primary frame and at least one secondary frame, the primary frame records sports and health data detected within a second time period, the secondary frame records sports and health data detected within a third time period, the second time period is a corresponding time period obtained by adding a previous primary frame of the primary frame, the secondary frame, and the specified time interval to the start time of the specified time period, and the third time period is a time period obtained by adding the specified time interval to an end time of a previous primary frame of the secondary frame or to an end time of the secondary frame, where the end time is used as a start time.

With reference to the first possible implementation of the fifth aspect, in a second possible implementation of the fifth aspect, the specified time interval is a time corresponding to one primary frame or secondary frame.

With reference to the fifth aspect, the first possible implementation of the fifth aspect, or the second possible implementation of the fifth aspect, in a third possible implementation of the fifth aspect, the specified time period is divided into at least one time zone, the logical pages are in a one-to-one correspondence with the time zones in order, the time zone is recorded in a field of a timestamp of a corresponding logical page, and an accumulated time period of the timestamp is the specified time period such that the second device determines a lost logical page of the sports and health data according to the timestamp.

With reference to the fifth aspect, the first possible implementation of the fifth aspect, the second possible implementation of the fifth aspect, or the third possible implementation of the fifth aspect, in a fourth possible implementation of the fifth aspect, the transmitter includes a receiving apparatus and a sending apparatus, where the receiving apparatus receives a retransmission request message sent by the second device, where content of the retransmission request message is empty, and the retransmission request message is used to indicate that the second device has not received sports and health data corresponding to a last logical page, or the retransmission request message carries a field of the last logical page, and the field of the last logical page is used to instruct the first device to retransmit sports and health data corresponding to the last logical page, and the sending apparatus resends the sports and health data on the last logical page to the second device according to an indication of the retransmission request message received by the receiving apparatus.

With reference to the fifth aspect, the first possible implementation of the fifth aspect, the second possible implementation of the fifth aspect, the third possible implementation of the fifth aspect, or the fourth possible implementation of the fifth aspect, in a fifth possible implementation of the fifth aspect, the processor further controls the transmitter according to the data storage structure to directly transmit the sports and health data within the specified time period to the second device, or the processor controls the memory according to the data storage structure to store the sports and health data within the specified time period and further controls the transmitter to transmit the sports and health data to the second device.

According to a sixth aspect, the present disclosure provides a second device, where the second device includes a receiving apparatus configured to receive, in a second device, sports and health data that is sent by a first device according to a particular data storage structure, where the particular data storage structure is divided into at least one logical page, each logical page includes at least one data frame group, each data frame group includes one primary frame and at least one secondary frame, the primary frame records sports and health data detected within a first time period, and the secondary frame records sports and health data detected within a second time period.

With reference to the sixth aspect, in a first possible implementation of the sixth aspect, the logical page carries a timestamp, the timestamp records a start time of sports and health data stored on the logical page, and each data frame group includes one primary frame and at least one secondary frame. The second device includes a processor and a sender, where the processor is configured to obtain, in the second device, a system time corresponding to the second device, a start time corresponding to a timestamp on the last logical page, and a sum of quantities of primary frames and secondary frames on the last logical page. The processor is further configured to determine, in the second device, whether a difference between the system time corresponding to the second device and the start time corresponding to the timestamp on the last logical page is equal to a product of the sum of the quantities of the primary frames and the secondary frames on the last logical page and the second time period, and the sender is configured to send, in the second device, a retransmission request message to the first device when the second device determines that the difference between the system time corresponding to the second device and the start time corresponding to the timestamp on the last logical page is not equal to the product of the sum of the quantities of the primary frames and the secondary frames on the last logical page and the second time period, where the retransmission request message is used to indicate that the second device has not received sports and health data on the last logical page.

According to a seventh aspect, the present disclosure provides a data storage structure, where the data storage structure is used by a first device to store sports and health data that is within a specified time period and that is detected by the first device, where the data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period.

With reference to the seventh aspect, in a first possible implementation of the seventh aspect, each logical page includes at least one data frame group, each data frame group includes one primary frame and at least one secondary frame, the primary frame records sports and health data detected within a second time period, the secondary frame records sports and health data detected within a third time period, the second time period is a corresponding time period obtained by adding a previous primary frame of the primary frame, the secondary frame, and the specified time interval to the start time of the specified time period, and the third time period is a time period obtained by adding the specified time interval to an end time of a previous primary frame of the secondary frame or to an end time of the secondary frame, where the end time is used as a start time.

With reference to the first possible implementation of the seventh aspect, in a second possible implementation of the seventh aspect, the specified time interval is a time corresponding to one primary frame or secondary frame.

For the data transmission method and apparatus, and the first device that are provided in the present disclosure, the first device first stores, according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and the specified time interval to a start time of the specified time period, and then transmits at least some of the sports and health data within the specified time period to a second device according to the data storage structure. Compared with storing sports and health data by a current wearable device per fixed unit time, in the present disclosure, each data frame in the first device stores the sports and health data detected within the first time period, sports and health data within the corresponding time period obtained by adding the previous data frame of the data frame and the specified time interval to the start time of the specified time period can be stored in the data frame, that is, a last data frame can store sports and health data detected within a preset time, and the sports and health data is transmitted to a second device such that the second device can obtain the last data frame, that is, all sports and health data within the specified time period can be obtained. Therefore, accuracy of analyzing sports and health data can be improved.

BRIEF DESCRIPTION OF DRAWINGS

To describe the technical solutions in the present disclosure more clearly, the following briefly describes the accompanying drawings required for describing the present disclosure. The accompanying drawings in the following description show merely some embodiments of the present disclosure, and a person of ordinary skill in the art may still derive other drawings from these accompanying drawings without creative efforts.

FIG. 3 shows a storage and transmission format of sports and health data according to an embodiment of the present disclosure;

DESCRIPTION OF EMBODIMENTS

The following clearly and completely describes the technical solutions in the embodiments of the present disclosure with reference to the accompanying drawings in the embodiments of the present disclosure. The described embodiments are merely some but not all of the embodiments of the present disclosure. All other embodiments obtained by a person of ordinary skill in the art based on the embodiments of the present disclosure without creative efforts shall fall within the protection scope of the present disclosure.

Figure 1:
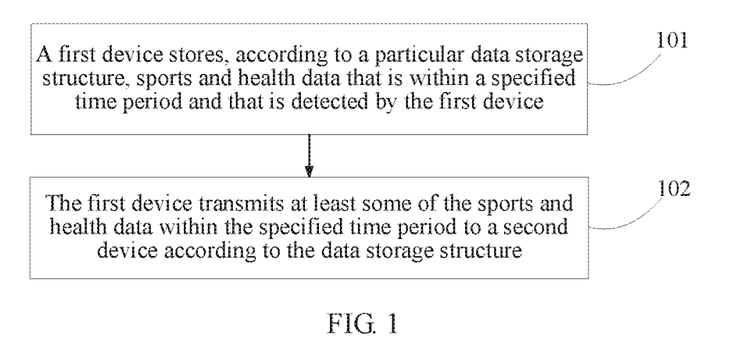
FIG. 1 is a flowchart of a data transmission method according to an embodiment of the present disclosure.

An embodiment of the present disclosure provides a data transmission method in order to improve accuracy of analyzing sports and health data of a user. As shown in FIG. 1, the method includes the following steps.

Step 101: A first device stores, according to a particular data storage structure, sports and health data that is within a specified time period and that is detected by the first device.

The particular data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period.

For this embodiment of the present disclosure, the first device may be a wearable device, another storage device, or the like. For example, the first device may be a smart band, a smartwatch, smart glasses, or the like.

For this embodiment of the present disclosure, a logical page is a particular data storage structure, and the logical page includes a page header and a data part. The page header includes a logical number of the logical page, data overflow, a status of the logical page, a byte quantity of a data frame, a timestamp, and a reserved bit.

For this embodiment of the present disclosure, the data frame is a protocol data unit at a data link layer, and the data frame includes three parts a frame header, a data part, and a frame trailer. The frame header and the frame trailer include some necessary control information such as synchronization information, address information, and error control information. The data part includes data transmitted from a network layer. In this embodiment of the present disclosure, the first device stores, using the data frame, sports and health data in storage space corresponding to the smart device. The storage space of the first device includes multiple data frames.

For this embodiment of the present disclosure, the sports and health data may be a quantity of walking steps of a user within a time period, a quantity of heartbeats within a time period, and consumed sports calories within a time period.

For this embodiment of the present disclosure, the first time period may be preconfigured by the first device, or may be preconfigured by a user. This is not limited in this embodiment of the present disclosure.

Step 102: The first device transmits at least some of the sports and health data within the specified time period to a second device according to the data storage structure.

For this embodiment of the present disclosure, the first device may be a wearable device such as a smart band, a smartwatch, or smart glasses. Because wearable devices may be some devices having relatively small storage space and screens, and the devices are inconvenient for a user to observe, the wearable device may send the sports and health data of the user to user equipment such as a mobile phone in order to observe, store, and analyze the sports and health data conveniently.

For this embodiment of the present disclosure, the first device may choose to send a part of the sports and health data of the user stored by the first device to the second device such that the second device analyzes sports and health data of the user within a particular time period according to the part of the sports and health data transmitted by the first device.

In the data transmission method provided in this embodiment of the present disclosure, a first device first stores, according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and the specified time interval to a start time of the specified time period, and then transmits at least some of the sports and health data within the specified time period to a second device according to the data storage structure. Compared with storing sports and health data by a current wearable device per fixed unit time, in this embodiment of the present disclosure, each data frame in the first device stores the sports and health data detected within the first time period, sports and health data within the corresponding time period obtained by adding the previous data frame of the data frame and the specified time interval to the start time of the specified time period can be stored in the data frame, that is, a last data frame can store sports and health data detected within a preset time, and the sports and health data is transmitted to a second device such that the second device can obtain the last data frame, that is, all sports and health data within the specified time period can be obtained. Therefore, accuracy of analyzing sports and health data can be improved.

Figure 2:
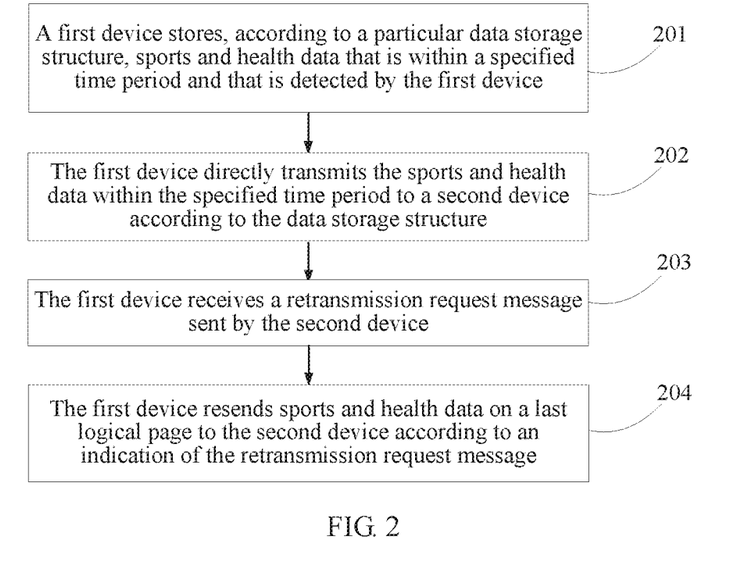
FIG. 2 is a flowchart of another data transmission method according to an embodiment of the present disclosure.

In specific descriptions of the method shown in FIG. 1, an embodiment of the present disclosure provides another data transmission method. As shown in FIG. 2, the method includes the following steps.

Step 201: A first device stores, according to a particular data storage structure, sports and health data that is within a specified time period and that is detected by the first device.

The particular data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period.

Each logical page includes at least one data frame group, each data frame group includes one primary frame and at least one secondary frame, the primary frame records sports and health data detected within a second time period, the secondary frame records sports and health data detected within a third time period, the second time period is a corresponding time period obtained by adding a previous primary frame of the primary frame, the secondary frame, and the specified time interval to the start time of the specified time period, and the third time period is a time period obtained by adding the specified time interval to an end time of a previous primary frame of the secondary frame or to an end time of the secondary frame, where the end time is used as a start time. In this embodiment of the present disclosure, the specified time interval is a time corresponding to one primary frame or secondary frame.

The specified time period is divided into at least one time zone, the logical pages are in a one-to-one correspondence with the time zones in order, the time zone is recorded in a field of a timestamp of a corresponding logical page, and an accumulated time period of the timestamp is the specified time period such that the second device determines a lost logical page of the sports and health data according to the timestamp.

For this embodiment of the present disclosure, the first device may be a wearable device, another storage device, or the like. For example, the first device may be a smart band, a smartwatch, smart glasses, or the like.

For this embodiment of the present disclosure, the first device may configure corresponding storage bytes for the logical page. For example, each logical page may occupy 1024 bytes, and if storage space of the first device is 1 megabyte (MB), the storage space corresponding to the first device may be divided into 1024 logical pages.

For this embodiment of the present disclosure, a logical page is a particular data storage structure, and the logical page includes a page header and a data part. The page header includes a logical number of the logical page, data overflow, a status of the logical page, a byte quantity of a data frame, a timestamp, and a reserved bit.

For this embodiment of the present disclosure, the data frame is a protocol data unit at a data link layer, and the data frame includes three parts a frame header, a data part, and a frame trailer. The frame header and the frame trailer include some necessary control information such as synchronization information, address information, and error control information. The data part includes data transmitted from a network layer. In this embodiment of the present disclosure, the first device stores, using the data frame, sports and health data in storage space corresponding to the smart device. The storage space of the first device includes multiple data frames.

For this embodiment of the present disclosure, the data frames in the storage space corresponding to the first device may be classified into a sports state and a sleep state, and the first device may configure corresponding storage space for the primary frame and the secondary frame. For example, one data frame group includes one primary frame and one secondary frame. One primary frame may occupy storage space of 75 bits, and one secondary frame may occupy storage space of 53 bits. If one logical page occupies 1024 bytes, one logical page may include 63 groups of data frames, as shown in FIG. 3.

For this embodiment of the present disclosure, the first device may estimate, according to an athletic ability within a time period of the user, sports and health data that can be stored by the first device within the time period, and configure storage space for the primary frame and the secondary frame. For example, when a user does sports, a maximum quantity of calories consumed by the user within one day is 33554431, and occupied storage space is 25 bits, a maximum quantity of sports steps of the user within one day is 131071, and occupied storage space is 17 bits, a longest sports distance of the user within one day is 524287 meters, and occupied storage space is 19 bits, a quantity of stories that the user can climb within one day is 16383, and occupied storage space is 14 bits, a maximum quantity of rope skipping times of the user within one day is 32767, and occupied storage space is 15 bits, as shown in Table 1.

TABLE 1

| Data type | Single day | | Each minute | |
|---|---|---|---|---|
| | Recommended value | Limiting value | Recommended value | Limiting value |
| Consumed sports calories | 24 bits (0 to 16777215, unit: calorie) | 25 bits (0 to 33554431, unit: calorie) | 14 bits (0 to 16383, unit: calorie) | 15 bits (0 to 32767, unit: calorie) |
| Consumed static calories | 21 bits (0 to 2097151, unit: calorie) | 22 bits (0 to 4194303, unit: calorie) | 11 bits (0 to 2047, unit: calorie) | 12 bits (0 to 4095, unit: calorie) |
| Quantity of sports steps (running/walking/mountain climbing) | 17 bits (0 to 131071, unit: step) | 17 bits (0 to 131071, unit: step) | 9 bits (0 to 511, unit: step) | 10 bits (0 to 1023, unit: step) |
| Sports distance (riding/walking/running) | 18 bits (0 to 262143, unit: meter) | 19 bits (0 to 524287, unit: meter) | 10 bits (0 to 1023, unit: meter) | 10 bits (0 to 1023, unit: meter) |
| Quantity of climbed stories | 13 bits (0 to 8191, unit: story) | 14 bits (0 to 16383, unit: story) | 4 bits (0 to 15, unit: story) | 5 bi (0 to 31, unit: story) |
| Quantity of rope skipping times | 14 bits (0 to 16383, unit: times) | 15 bits (0 to 32767, unit: times) | 9 bits (0 to 511, unit: times) | 10 bits (0 to 1023, unit: times) |
| Respiratory rate | . . . | . . . | 7 bits (0 to 127, unit: times) | . . . |
| Body temperature | . . . | . . . | 6 bits (0 to 63, unit: Celsius degree) | . . . |
| Heart rate | . . . | . . . | 8 bits (0 to 255, unit: times) | . . . |

For this embodiment of the present disclosure, if each data frame group includes one primary frame and one secondary frame, the primary frame records sports and health data stored within a corresponding time period obtained by adding a previous primary frame of the primary frame, the secondary frame, and the specified time interval to a start time of the specified time period, and the secondary frame records sports and health data stored within a time period obtained by adding a specified time interval to an end time of a previous primary frame of the secondary frame or to an end time of the secondary frame, where the end time is used as a start time. For example, if a specified time interval is one minute, sports and health data included in a primary frame part in an $M^{th}$ data frame group is an accumulated value from 00:00 to 10:00, a secondary frame part corresponding to the primary frame part includes sports and health data obtained from 10:00 to 10:01, sports and health data included in a primary frame part of an $(M+1)^{th}$ data frame group is an accumulated value from 00:00 to 10:02, and a secondary frame part corresponding to the primary frame part includes sports and health data obtained from 10:02 to 10:03.

Step 202: The first device directly transmits the sports and health data within the specified time period to a second device according to the data storage structure.

Optionally, the first device first stores the sports and health data within the specified time period according to the data storage structure, and then transmits the sports and health data within the specified time period to the second device.

For this embodiment of the present disclosure, the smart device may be a smart device such as a smartphone, a tablet, or a computer that can perform storage and analysis.

For this embodiment of the present disclosure, the first device stores sports and health data according to a particular storage structure, that is, stores sports and health data according to a storage structure of a logical page, and transmits the sports and health data according to a data structure of the logical page. Therefore, format conversion may be avoided before the sports and health data is transmitted. That is, conversion from a storage structure to a transmission structure can be avoided, and complexity of transmitting sports and health data can be further reduced.

For this embodiment of the present disclosure, the first device transmits at least some of the sports and health data within the specified time period to the second device such that the second device receives and stores sports and health data within an optional time period, and the second device analyzes the sports and health data within the optional time period. This can improve flexibility of analyzing sports and health data.

Step 203: The first device receives a retransmission request message sent by the second device.

The retransmission request message is empty, and the retransmission request message is used to indicate that the second device has not received sports and health data corresponding to a last logical page. Alternatively, the retransmission request message carries a field of a last logical page, and the field of the last logical page is used to instruct the first device to retransmit sports and health data corresponding to the last logical page.

For this embodiment of the present disclosure, the first device sends the sports and health data to the second device in a wireless transmission manner. In this embodiment of the present disclosure, the wireless transmission manner may be a BLUETOOTH transmission manner, a WI-FI transmission manner, or the like.

For this embodiment of the present disclosure, because a channel for wireless transmission is a weak channel, and interferes with a transmitted signal on some radio wave bands, in a process in which the first device sends the sports and health data to the second device in a wireless transmission manner, some sports and health data is lost. That is, user equipment may not receive entire sports and health data.

Figure 4:
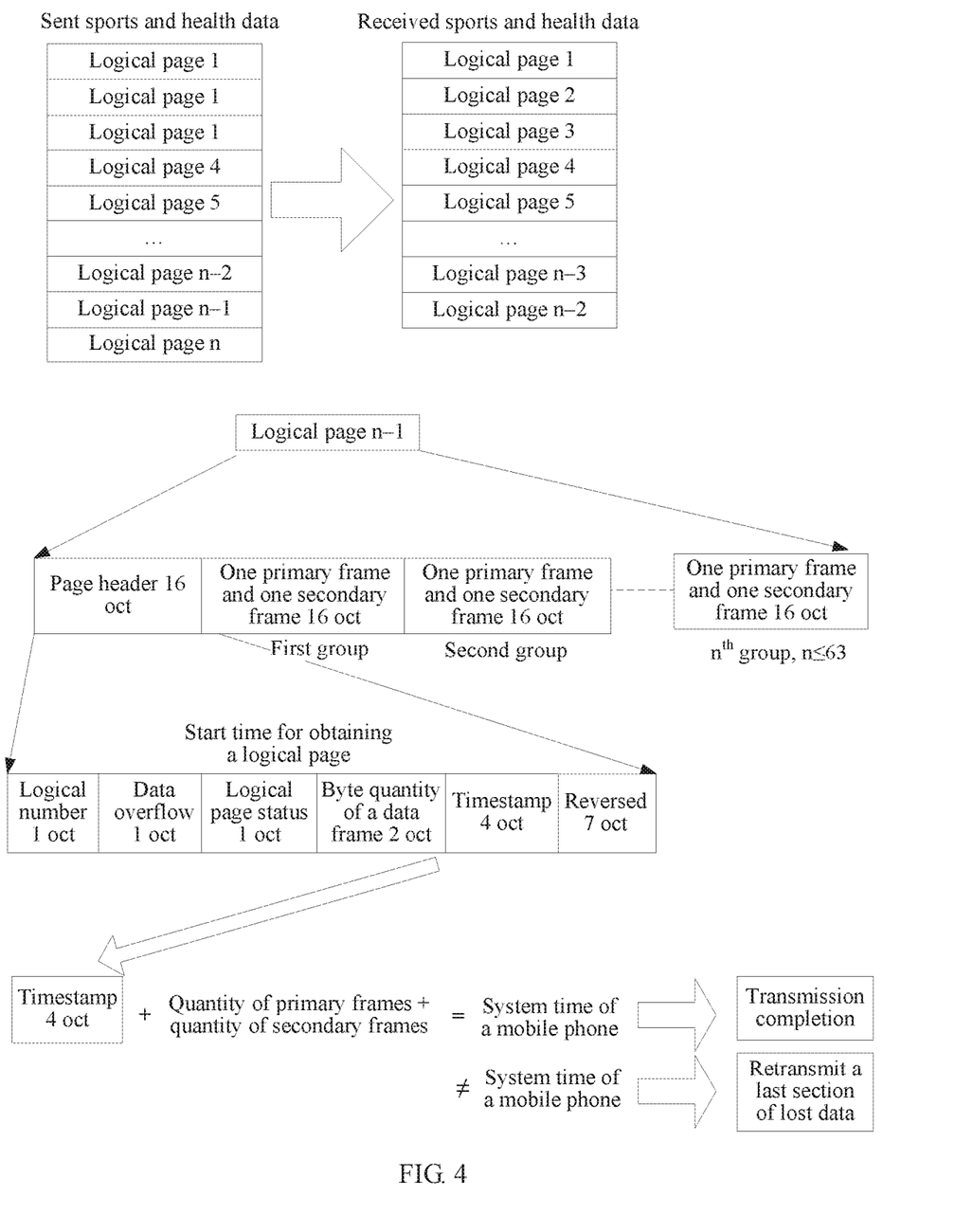
FIG. 4 shows processing of loss of a last logical page in a transmission process according to an embodiment of the present disclosure.

For this embodiment of the present disclosure, after receiving the sports and health data sent by the first device, the second device determines whether the sports and health data, which is sent by the first device, on the last logical page is lost in the transmission process. Further, if the first device sends the sports and health data within the specified time period to the second device, the second device obtains a timestamp of the received last logical page, and a sum of a quantity of primary frames and a quantity of secondary frames on the last logical page, and a difference between a product of a third time period and the sum of the quantity of the primary frames and the quantity of the secondary frames on the last logical page, and the timestamp on the last logical page is equal to the specified time period, the last logical page is not lost in the transmission process. If the first device sends all stored sports and health data to the second device, the second device obtains a system time currently corresponding to the second device, a timestamp carried on the last logical page received by the second device, and the sum of quantities of the primary frames and the secondary frames on the last logical page. Further, if a difference between the system time currently corresponding to the second device and a time corresponding to a timestamp carried on a last logical page received by the second device is not equal to the product of the third time period and the sum of the quantity of the primary frames and the quantity of the secondary frames on the last logical page received by the second device, the last logical page is lost in the transmission process. That is, a retransmission request message is sent to the first device, and the retransmission request message carries a field of the last logical page, as shown in FIG. 4.

Step 204: The first device resends sports and health data on a last logical page to the second device according to an indication of the retransmission request message.

For this embodiment of the present disclosure, when the first device receives the retransmission request message that is sent by the second device to the first device, the first device resends the sports and health data on the last logical page to the second device such that the second device can obtain all sports and health data stored within the specified time period. Therefore, sports and health data of a user can be accurately analyzed, and accuracy of analyzing the sports and health data can be further improved.

In the data transmission method provided in this embodiment of the present disclosure, a first device first stores, according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and the specified time interval to a start time of the specified time period, and then transmits at least some of the sports and health data within the specified time period to a second device according to the data storage structure. Compared with storing sports and health data by a current wearable device per fixed unit time, in this embodiment of the present disclosure, each data frame in the first device stores the sports and health data detected within the first time period, sports and health data within the corresponding time period obtained by adding the previous data frame of the data frame and the specified time interval to the start time of the specified time period can be stored in the data frame, that is, a last data frame can store sports and health data detected within a preset time, and the sports and health data is transmitted to a second device such that the second device can obtain the last data frame, that is, all sports and health data within the specified time period can be obtained. Therefore, accuracy of analyzing sports and health data can be improved.

Further, in the data transmission method provided in this embodiment of the present disclosure, a first device stores sports and health data according to a particular storage structure, that is, stores sports and health data according to a storage structure of a logical page, and transmits the sports and health data according to a data structure of the logical page. Therefore, format conversion may be avoided before the sports and health data is transmitted. That is, conversion from a storage structure to a transmission structure can be avoided, and complexity of transmitting sports and health data can be further reduced. The first device transmits at least some of the sports and health data within the specified time period to the second device such that the second device receives and stores sports and health data within an optional time period, and the second device analyzes the sports and health data within the optional time period. This can improve flexibility of analyzing sports and health data. When the first device receives a retransmission request message that is sent by the second device to the first device, the first device resends sports and health data on a last logical page to the second device such that the second device can obtain all sports and health data stored within the specified time period. Therefore, sports and health data of a user can be accurately analyzed, and accuracy of analyzing the sports and health data can be further improved.

Figure 5:
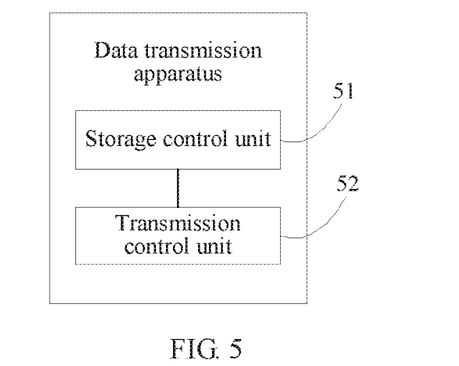
FIG. 5 is a schematic structural diagram of a data transmission apparatus according to an embodiment of the present disclosure.

Further, in implementation of the methods shown in FIG. 1 and FIG. 2, an embodiment of the present disclosure further provides a data transmission apparatus. The apparatus may be located in a first device, and is configured to improve accuracy of analyzing sports and health data. As shown in FIG. 5, the apparatus includes a storage control unit 51 and a transmission control unit 52.

The storage control unit 51 stores, according to a particular data storage structure, sports and health data that is within a specified time period and that is detected by the first device.

The particular data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period.

Each logical page includes at least one data frame group, each data frame group includes one primary frame and at least one secondary frame, the primary frame records sports and health data detected within a second time period, the secondary frame records sports and health data detected within a third time period, the second time period is a corresponding time period obtained by adding a previous primary frame of the primary frame, the secondary frame, and the specified time interval to the start time of the specified time period, and the third time period is a time period obtained by adding the specified time interval to an end time of a previous primary frame of the secondary frame or to an end time of the secondary frame, where the end time is used as a start time.

The specified time interval is a time corresponding to one primary frame or secondary frame.

The specified time period is divided into at least one time zone, the logical pages are in a one-to-one correspondence with the time zones in order, the time zone is recorded in a field of a timestamp of a corresponding logical page, and an accumulated time period of the timestamp is the specified time period such that the second device determines a lost logical page of the sports and health data according to the timestamp.

The transmission control unit 52 controls a transmitter according to the data storage structure to transmit at least some of the sports and health data within the specified time period to a second device.

Figure 6:
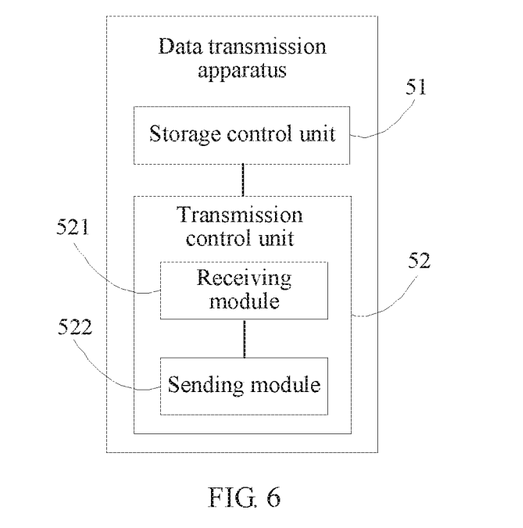
FIG. 6 is a schematic structural diagram of another data transmission apparatus according to an embodiment of the present disclosure.

Further, as shown in FIG. 6, the transmission control unit 52 further includes a receiving module 521 and a sending module 522.

The receiving module 521 is configured to receive a retransmission request message sent by the second device.

Content of the retransmission request message is empty, and the retransmission request message is used to indicate that the second device has not received sports and health data corresponding to a last logical page, or the retransmission request message carries a field of a last logical page, and the field of the last logical page is used to instruct the apparatus to retransmit sports and health data corresponding to the last logical page.

The sending module 522 is configured to resend the sports and health data on the last logical page to the second device according to an indication of the retransmission request message received by the receiving module 521.

The apparatus directly transmits the sports and health data within a specified time period to the second device according to the data storage structure. Alternatively, the apparatus first stores the sports and health data within the specified time period according to the data storage structure and then transmits the sports and health data within the specified time period to the second device.

The apparatus is a first device.

For the data transmission apparatus provided in this embodiment of the present disclosure, the first device first stores, according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and the specified time interval to a start time of the specified time period, and then transmits at least some of the sports and health data within the specified time period to a second device according to the data storage structure. Compared with storing sports and health data by a current wearable device per fixed unit time, in this embodiment of the present disclosure, each data frame in the first device stores the sports and health data detected within the first time period, sports and health data within the corresponding time period obtained by adding the previous data frame of the data frame and the specified time interval to the start time of the specified time period can be stored in the data frame, that is, a last data frame can store sports and health data detected within a preset time, and the sports and health data is transmitted to a second device such that the second device can obtain the last data frame, that is, all sports and health data within the specified time period can be obtained. Therefore, accuracy of analyzing sports and health data can be improved.

Further, for the data transmission apparatus provided in this embodiment of the present disclosure, the first device stores sports and health data according to a particular storage structure, that is, stores sports and health data according to a storage structure of a logical page, and transmits the sports and health data according to a data structure of the logical page. Therefore, format conversion may be avoided before the sports and health data is transmitted. That is, conversion from a storage structure to a transmission structure can be avoided, and complexity of transmitting sports and health data can be further reduced. The first device transmits at least some of the sports and health data within the specified time period to the second device such that the second device receives and stores sports and health data within an optional time period, and the second device analyzes the sports and health data within the optional time period. This can improve flexibility of analyzing sports and health data. When the first device receives a retransmission request message that is sent by the second device to the first device, the first device resends sports and health data on a last logical page to the second device such that the second device can obtain all sports and health data stored within the specified time period. Therefore, sports and health data of a user can be accurately analyzed, and accuracy of analyzing the sports and health data can be further improved.

It should be noted that, for other corresponding descriptions corresponding to units in the data transmission apparatus provided in this embodiment of the present disclosure, refer to corresponding descriptions in FIG. 1 and FIG. 2, and details are not described herein again.

Figure 7:
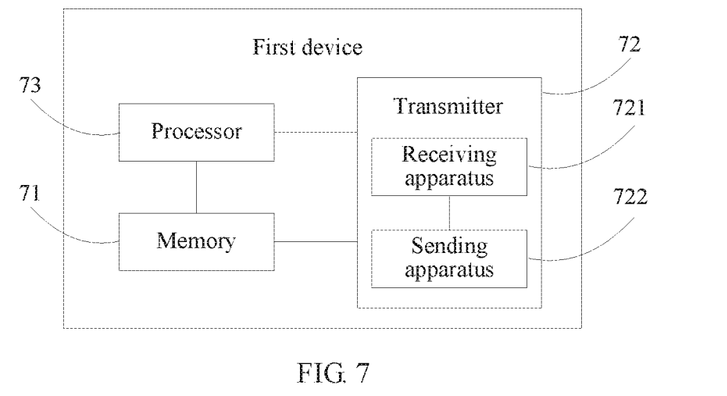
FIG. 7 is a schematic structural diagram of a data transmission device according to an embodiment of the present disclosure.

Further, an embodiment of the present disclosure further provides a data transmission device. As shown in FIG. 7, the data transmission device is a first device. The first device includes a memory 71, a transmitter 72, and a processor 73, and the processor 73 is connected to the memory 71 and the transmitter 72 using a data bus (not shown).

The processor 73 is configured to store, in the memory 71 according to a particular data storage structure, sports and health data that is within a specified time period and that is detected by the first device.

The particular data storage structure is divided into at least one logical page, each logical page includes at least one data frame, each data frame records sports and health data detected within a first time period, and the first time period is a corresponding time period obtained by adding a previous data frame of the data frame and a specified time interval to a start time of the specified time period.

Each logical page includes at least one data frame group, each data frame group includes one primary frame and at least one secondary frame, the primary frame records sports and health data detected within a second time period, the secondary frame records sports and health data detected within a third time period, the second time period is a corresponding time period obtained by adding a previous primary frame of the primary frame, the secondary frame, and the specified time interval to the start time of the specified time period, and the third time period is a time period obtained by adding the specified time interval to an end time of a previous primary frame of the secondary frame or to an end time of the secondary frame, where the end time is used as a start time.

The specified time interval is a time corresponding to one primary frame or secondary frame.

The specified time period is divided into at least one time zone, the logical pages are in a one-to-one correspondence with the time zones in order, the time zone is recorded in a field of a timestamp of a corresponding logical page, and an accumulated time period of the timestamp is the specified time period such that a second device determines a lost logical page of the sports and health data according to the timestamp.

The processor 73 is configured to transmit at least some of the sports and health data within the specified time period to the second device according to the data storage structure using the transmitter 72.

Further, the transmitter 72 includes a receiving apparatus 721 and a sending apparatus 722.

The receiving apparatus 721 receives a retransmission request message sent by the second device.

Content of the retransmission request message is empty, and the retransmission request message is used to indicate that the second device has not received sports and health data corresponding to a last logical page, or the retransmission request message carries a field of a last logical page, and the field of the last logical page is used to instruct the first device to retransmit sports and health data corresponding to the last logical page.

The sending apparatus 722 resends the sports and health data on the last logical page to the second device according to an indication of the retransmission request message received by the receiving apparatus 721.

The processor 73 further controls the transmitter 72 according to the data storage structure to directly transmit the sports and health data within the specified time period to the second device, or the processor 73 controls the memory 71 according to the data storage structure to store the sports and health data within the specified time period, and further controls the transmitter 72 to transmit the sports and health data to the second device.

For the first device provided in this embodiment of the present disclosure, the first device first stores, according to a particular data storage structure, sports and health data that is within a specified time period and that is detected by the first device, where the particular data storage structure is divided into at least one logical page, each logical page includes at least one data frame, each data frame records sports and health data detected within a first time period, and the first time period is a corresponding time period obtained by adding a previous data frame of the data frame and the specified time interval to a start time of the specified time period, and then transmits at least some of the sports and health data within the specified time period to a second device according to the data storage structure. Compared with storing sports and health data by a current wearable device per fixed unit time, in this embodiment of the present disclosure, each data frame in the first device stores the sports and health data detected within the first time period, sports and health data within the corresponding time period obtained by adding the previous data frame of the data frame and the specified time interval to the start time of the specified time period can be stored in the data frame, that is, a last data frame can store sports and health data detected within a preset time, and the sports and health data is transmitted to a second device such that the second device can obtain the last data frame, that is, all sports and health data within the specified time period can be obtained. Therefore, accuracy of analyzing sports and health data can be improved.

Further, for the first device provided in this embodiment of the present disclosure, the first device stores sports and health data according to a particular storage structure, that is, stores sports and health data according to a storage structure of a logical page, and transmits the sports and health data according to a data structure of the logical page. Therefore, format conversion may be avoided before the sports and health data is transmitted. That is, conversion from a storage structure to a transmission structure can be avoided, and complexity of transmitting sports and health data can be further reduced. The first device transmits at least some of the sports and health data within the specified time period to the second device such that the second device receives and stores sports and health data within an optional time period, and the second device analyzes the sports and health data within the optional time period. This can improve flexibility of analyzing sports and health data. When the first device receives a retransmission request message that is sent by the second device to the first device, the first device resends sports and health data on a last logical page to the second device such that the second device can obtain all sports and health data stored within the specified time period. Therefore, sports and health data of a user can be accurately analyzed, and accuracy of analyzing the sports and health data can be further improved.

The data transmission apparatus provided in this embodiment of the present disclosure may implement the method embodiments provided above. For specific function implementation, refer to the descriptions in the method embodiments. Details are not described herein again. The data transmission method and apparatus that are provided in the embodiments of the present disclosure are applicable to storage, transmission, and error correction of sports and health data in order to obtain sports and health data within a specified time period. However, the present disclosure is not limited thereto.

A person of ordinary skill in the art may understand that all or some of the processes of the methods in the embodiments may be implemented by a computer program instructing relevant hardware. The program may be stored in a computer readable storage medium. When the program runs, the processes of the methods in the embodiments are performed. The foregoing storage medium may include a magnetic disk, an optical disc, a read-only memory (ROM), or a random access memory (RAM).

The foregoing descriptions are merely specific embodiments of the present disclosure, but are not intended to limit the protection scope of the present disclosure. Any variation or replacement readily figured out by a person skilled in the art within the technical scope disclosed in the present disclosure shall fall within the protection scope of the present disclosure. Therefore, the protection scope of the present disclosure shall be subject to the protection scope of the claims.

What is claimed is:

1. A data transmission method, comprising:
storing, by a first device according to a particular data storage structure, sports and health data within a specified time period that is detected by the first device, wherein the particular data storage structure is divided into at least one logical page, wherein each logical page comprises at least one data frame group, wherein each data frame group comprises a primary frame and a secondary frame, wherein the primary frame records sports and health data detected within a first time period, wherein the secondary frame records sports and health data detected within a second time period, wherein the first time period is a corresponding time period obtained by adding a previous primary frame of the primary frame, the secondary frame, and a specified time interval to a start time of the specified time period, wherein the second time period is a time period obtained by adding the specified time interval to an end time of a previous primary frame of the secondary frame or to an end time of the secondary frame, wherein the end time is used as the start time, and wherein the secondary frame corresponds to a different time period than the primary frame based on accumulation of a primary time period corresponding to the primary frame;

transmitting, by the first device, a first message including at least some of the sports and health data within the specified time period to a second device according to the data storage structure, wherein the first message includes a timestamp corresponding to a transmitted logical page;

receiving, by the first device, a retransmission request message from the second device when a product of the second time period and a sum of a quantity of primary frames of the transmitted logical page and a quantity of secondary frames of the transmitted logical page is not equal to a difference between a system time of the second device and the timestamp, wherein content of the retransmission request message is empty and the retransmission request message indicates that the second device has not received sports and health data corresponding to a last logical page, or wherein the retransmission request message carries a field of the last logical page and the field of the last logical page instructs the first device to retransmit the sports and health data corresponding to the last logical page; and resending, by the first device, the sports and health data on the last logical page to the second device according to an indication of the retransmission request message.

2. The data transmission method of claim 1, wherein the specified time interval is a time corresponding to one primary frame.

3. The data transmission method of claim 1, wherein the specified time interval is a time corresponding to one secondary frame.

4. The data transmission method of claim 1, wherein the specified time period is divided into at least one time zone, wherein the pages are in a one-to-one correspondence with the time zones in order, wherein the at least one time zone is recorded in a field of a timestamp of a corresponding logical page, and wherein an accumulated time period of the timestamp is the specified time period.

5. The data transmission method of claim 1, wherein transmitting the at least some of the sports and health data comprises directly transmitting, by the first device, the sports and health data within the specified time period to the second device according to the data storage structure.

6. The data transmission method of claim 1, wherein transmitting the at least some of the sports and health data comprises:
storing, by the first device, the sports and health data within the specified time period according to the data storage structure; and
transmitting the sports and health data within the specified time period to the second device.

7. A data transmission device, wherein the data transmission device is a first device, wherein the data transmission device comprises:
a bus;
a memory coupled to the bus;
a transmitter coupled to the bus; and
a processor coupled to the bus and configured to:
store, in the memory according to a particular data storage structure, sports and health data within a specified time period that is detected by the first device, wherein the particular data storage structure is divided into at least one logical page, wherein each logical page comprises at least one data frame group, wherein each data frame group comprises a primary frame and a secondary frame, wherein the primary frame records sports and health data detected within a first time period, wherein the secondary frame records sports and health data detected within a second time period, wherein the first time period is a corresponding time period obtained by adding a previous primary frame of the primary frame, the secondary frame, and a specified time interval to a start time of the specified time period, wherein the second time period is a time period obtained by adding the specified time interval to an end time of a previous primary frame of the secondary frame or to an end time of the secondary frame, wherein the end time is used as the start time, and wherein the secondary frame corresponds to a different time period than the primary frame based on accumulation of a primary time period corresponding to the primary frame;

transmit, using the transmitter, a first message including at least some of the sports and health data within the specified time period to a second device according to the data storage structure, wherein the first message includes a timestamp corresponding to a transmitted logical page;

receive, by the first device, a retransmission request message from the second device when a product of the second time period and a sum of a quantity of primary frames of the transmitted logical page and a quantity of secondary frames of the transmitted logical page is not equal to a difference between a system time of the second device and the timestamp, wherein content of the retransmission request message is empty and the retransmission request message indicates that the second device has not received sports and health data corresponding to a last logical page, or wherein the retransmission request message carries a field of the last logical page and the field of the last logical page instructs the first device to retransmit the sports and health data corresponding to the last logical page; and resend, by the first device, the sports and health data on the last logical page to the second device according to an indication of the retransmission request message.

8. The data transmission device of claim 7, wherein the specified time interval is a time corresponding to one primary frame.

9. The data transmission device of claim 7, wherein the specified time interval is a time corresponding to one secondary frame.

10. The data transmission device of claim 7, wherein the specified time period is divided into at least one time zone, wherein logical pages are in a one-to-one correspondence with time zones in order, wherein the at least one time zone is recorded in a field of a timestamp of a corresponding logical page, and wherein an accumulated time period of the timestamp is the specified time period.

11. The data transmission device of claim 7, wherein the processor is further configured to directly transmit, using the transmitter according to the data storage structure, the sports and health data within the specified time period to the second device.

12. The data transmission device of claim 7, wherein the processor is further configured to:
store, using the memory according to the data storage structure, the sports and health data within the specified time period; and transmit, using the transmitter, the sports and health data to the second device.

13. A first device, comprising:
a memory; and
a processor coupled to the memory and configured to:
store, in the memory according to a particular data storage structure, sports and health data within a specified time period that is detected by the first device, wherein the particular data storage structure is divided into at least one logical page, wherein each logical page comprises at least one data frame group, wherein each data frame group comprises a primary frame and a secondary frame, wherein the primary frame records sports and health data detected within a first time period, wherein the secondary frame records sports and health data detected within a second time period, wherein the first time period is a corresponding time period obtained by adding a previous primary frame of the primary frame, the secondary frame, and a specified time interval to a start time of the specified time period, wherein the second time period is a time period obtained by adding the specified time interval to an end time of a previous primary frame of the secondary frame or to an end time of the secondary frame, wherein the end time is used as the start time and wherein the secondary frame corresponds to a different time period than the primary frame based on accumulation of a primary time period corresponding to the primary frame;
transmit, by the first device, a first message including at least some of the sports and health data within the specified time period to a second device according to the data storage structure, wherein the first message includes a timestamp corresponding to a transmitted logical page;
receive, by the first device, a retransmission request message from the second device when a product of the second time period and a sum of a quantity of primary frames of the transmitted logical page and a quantity of secondary frames of the transmitted logical page is not equal to a difference between a system time of the second device and the timestamp, wherein content of the retransmission request message is empty and the retransmission request message indicates that the second device has not received sports and health data corresponding to a last logical page, or wherein the retransmission request message carries a field of the last logical page and the field of the last logical page instructs the first device to retransmit the sports and health data corresponding to the last logical page; and
resend, by the first device, the sports and health data on the last logical page to the second device according to an indication of the retransmission request message.

14. The first device of claim 13, wherein the specified time interval is a time corresponding to one primary frame.

15. The first device of claim 13, wherein the specified time interval is a time corresponding to one secondary frame.